[19] United States Patent
Angst et al.

[11] Patent Number: 4,974,457
[45] Date of Patent: Dec. 4, 1990

[54] APPARATUS AND METHOD FOR PROVIDING A PASSAGE IN A SEALING MEMBER OF A CONTAINER OF A FLUID SAMPLE

[75] Inventors: Heinz Angst; Albert Schär, both of Langenthal, Switzerland

[73] Assignee: Hightech Network S.C.I. AB, Malmö, Sweden

[21] Appl. No.: 337,476

[22] Filed: Apr. 13, 1989

[51] Int. Cl.⁵ ............................................. G01N 1/14
[52] U.S. Cl. ............................................. 73/863.081
[58] Field of Search ............... 73/863, 863.01, 863.81, 73/863.85, 864.01, 864.21, 864.23–864.25, 864.81, 864.85–864.87, 864.91, 863.81; 422/99, 100, 102; 215/355, 357–362, DIG. 3; 220/15, DIG. 17; 604/411

[56] References Cited

U.S. PATENT DOCUMENTS

| 3,872,730 | 3/1975 | Ringrose et al. | 73/864.23 |
| 3,991,627 | 11/1978 | Laird et al. | 73/864.16 |
| 4,624,148 | 11/1986 | Averette | 73/864.21 |
| 4,713,974 | 12/1987 | Stone | 73/863.01 |
| 4,808,381 | 2/1989 | McGregor et al. | 422/100 |
| 4,815,625 | 3/1989 | Filhol et al. | 422/102 |

FOREIGN PATENT DOCUMENTS

| 126390 | 11/1984 | European Pat. Off. . |
| 221315 | 5/1987 | European Pat. Off. . |
| 0179660 | 9/1985 | Japan | 73/864.21 |
| 8705208 | 11/1987 | PCT Int'l Appl. . |
| 878504 | 10/1961 | United Kingdom . |

Primary Examiner—Robert Raevis
Attorney, Agent, or Firm—Laubscher, Presta & Laubscher

[57] ABSTRACT

The apparatus for providing a passage in a sealing member, in particular a stopper of a container of a fluid sample, by using a penetrating sleeve defining the passage, comprises a displaceable sticking tool. The latter comprises a spike with a pointed end. During operation the spike is inserted into the sleeve and brought into a position in which its pointed end protrudes through the front end of the sleeve. The spike together with the sleeve are then stuck through the sealing member. Subsequently, the spike is pulled out of the sleeve, while the sleeve is left inside the sealing member. In this way, the sleeve may be inserted into the sealing member along a predetermined path, while any cutting or shearing of particles off the sealing member may be avoided.

24 Claims, 5 Drawing Sheets

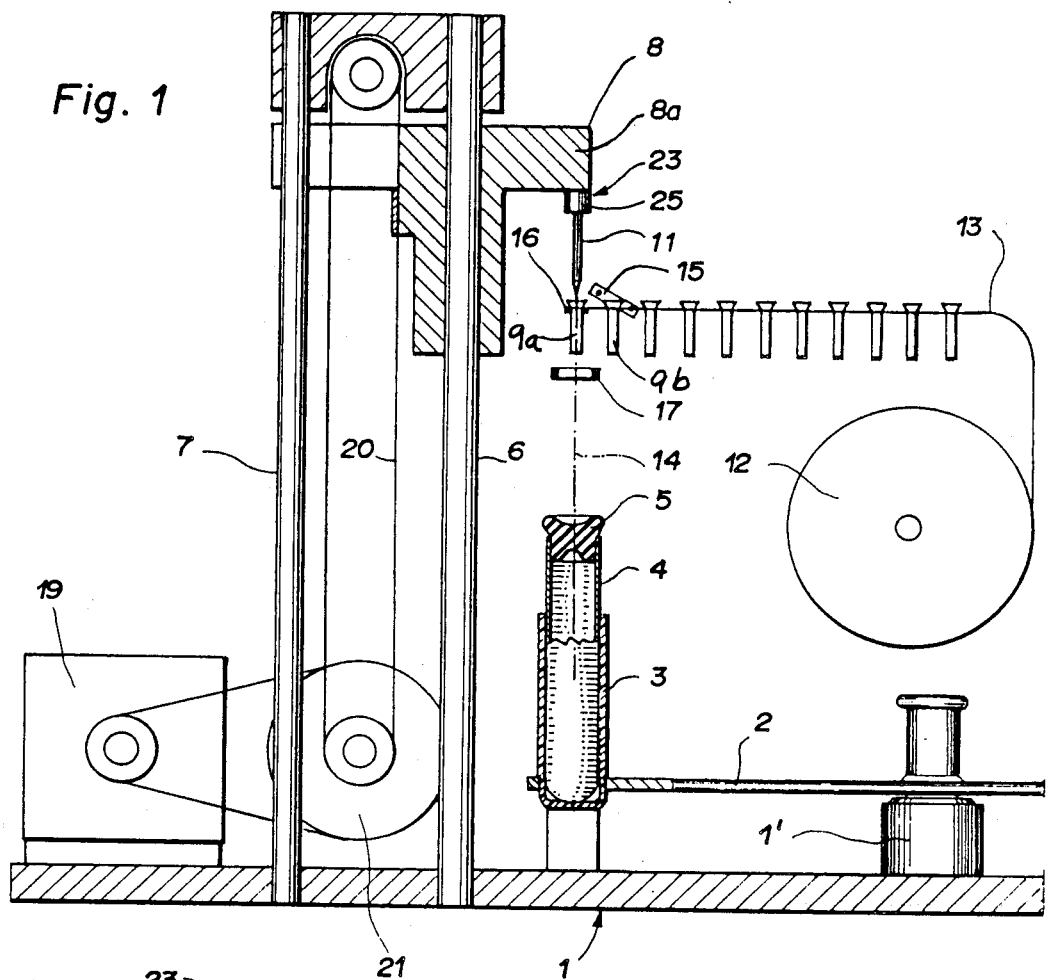
Fig. 1
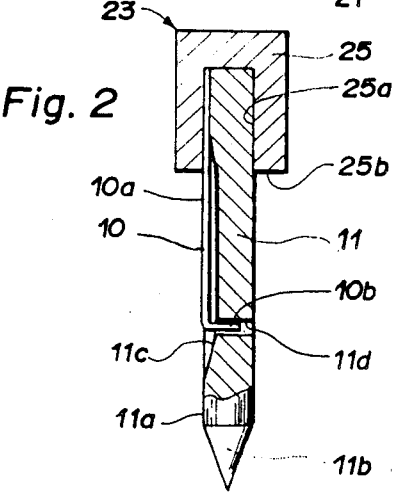
Fig. 2
Fig. 3

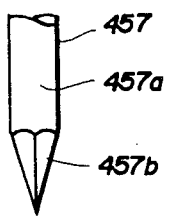
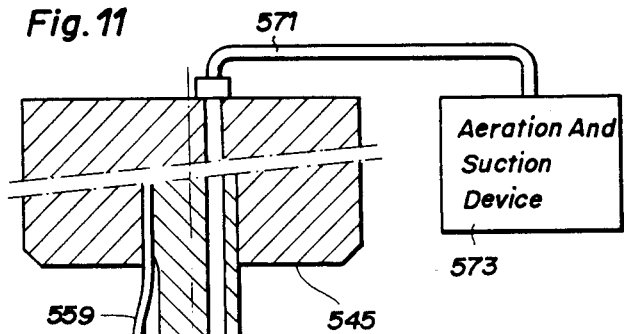
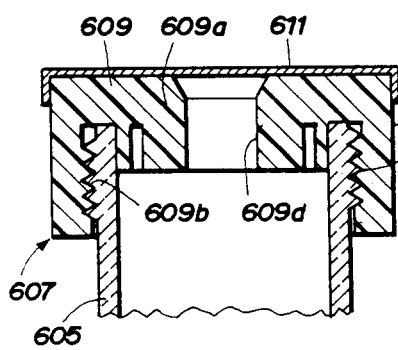
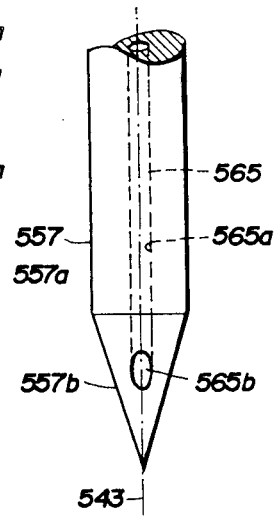
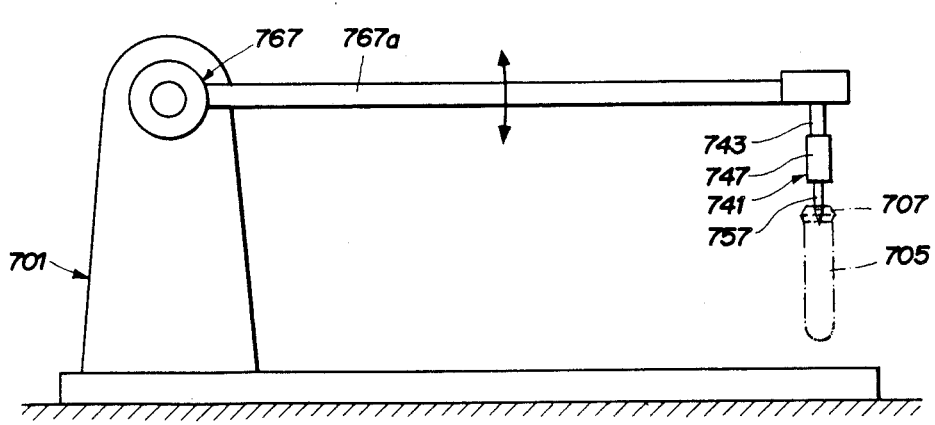

APPARATUS AND METHOD FOR PROVIDING A PASSAGE IN A SEALING MEMBER OF A CONTAINER OF A FLUID SAMPLE

BACKGROUND OF THE INVENTION

1. Field of the Invention

The present invention relates to an apparatus and a method for providing a passage in a sealing member of a container of a fluid sample, the passage being intended to allow the withdrawal of at least a portion of the fluid sample from the container, the latter being also referred to in the following as sample container. The invention also relates to a sleeve to be stuck or pierced through a sealing member of a sample container, whereby the sleeve —after having been inserted into the sealing member—defines said passage. Accordingly, the sleeve serves as a kind of cannula.

The sealing member may be a stopper consisting of an elastic deformable material, for instance of a rubber elastic material. The stopper may consist for instance of natural rubber and/or a synthetic plastic rubber such as silicon caoutchouc, polyisoprene or another more or less rubber elastic polymer such as a relatively elastic polyurethane. The stopper may also consist of another suitable, deformable material such as cork.

The sealing member, however, may also be a cap such as a screw cap. The screw cap may comprise a screw member having a central section provided with a through-going axial hole and a ring or tubular section provided with an inner thread screwed onto an outer thread of the sample container. The axial hole may then be closed by a covering foil applied to the outer, upper side or possibly on the inner, lower side of the screw member. The screw member may consist of a polymer to some extent elastically deformable but not as elastic as rubber. The screw member may consist for instance of a thermoplastic polymer such as polypropylene, polyethylene, polystyrene or relatively hard polyurethane. The foil may consist of a metallic material or possibly of one of the aforementioned thermoplastic polymers. The screw cap, however, may consist of a single piece including screw member and foil. The throughgoing hole could then be replaced by a blind hole bounded at one end by the foil, so that the foil will be constituted by a portion of said single piece, which may then have one of the aforementioned polymers as screw member material.

Normally, the fluid sample is at least in part and/or at least substantially liquid. More specifically, the fluid constituting the sample may comprise a body fluid, such as blood or blood serum or urine of a living human being or an animal. Accordingly, the sample may comprise a liquid containing dispersed solid particles and possibly dissolved gas, or fluid completely liquid.

The body fluid to be analyzed may have been introduced into the sample container in one of various ways before the sealing member has been provided with the sleeve defining said passage. If the sealing member consists of a stopper more or less rubber elastic, the body fluid may have been introduced into the sample container, for instance, by first producing a vacuum inside the container and then sticking a thin, needle-like cannula through the sealing member, to have the vacuum suck the fluid into the container through the cannula. After the fluid has been sucked into the container, the cannula is withdrawn from the sealing member, i.e. the stopper. The elasticity of the latter causes then the hole created before by the cannula to be closed so that the container now containing a body fluid will again be tightly sealed by the sealing member.

In case the sealing member is realized as screw cap, the body fluid may have been brought into the sample container while the latter was open. If the fluid has been introduced into the sample container, the latter will have been closed, of course, by means of the cap.

After the sealing member has been provided with a sleeve for creating the passage, the fluid sample or part thereof may be extracted from the container by means of a suction device comprising a fluid conduit, such as a hose, introduced into the passage. The extracted fluid may then be analyzed. Or, several portions of the fluid sample may be extracted, one after the other, and subjected to various procedures of analysis.

2. Description of the Prior Art

Relatively weak hoses are normally used as fluid conduits for sucking liquid fluid out of sample containers. Such hoses cannot be pushed directly through stoppers which consist of one of the previously specified materials, and are relatively thick. One could of course remove the stopper to make the fluid sample in the container accessible. This method, however, even though frequently used, has several drawbacks. There is the risk, for example, that a layer of the sample will adhere to the extracted stopper. The container usually consists of a thin-walled test glass tube and the stopper is firmly seated in the glass tube and additionally held in place by the partial vacuum created temporarily inside the tube while the stopper is displaced for opening the container. Therefore, the removal of the stopper generally requires considerable force and carries the risk that the air streaming abruptly into the container at the moment of stopper extraction will produce an aerosol mist comprising fine droplets of the liquid fluid. This and/or any possibly occuring jerk of the sample container may spray and/or spout droplets and/or drops out of the glass tube. The latter may even possibly break. If sample liquid adheres to the stopper or comes out of the sample container in any one of the other aforementioned ways, such liquid may contaminate devices and/or persons and cause serious dangers of infecting the concerned persons. Furthermore the removal of a stopper is relatively time-consuming and is—particular in consideration of the previously mentioned drawbacks—not easily feasible with an apparatus working fully automatically. Similar problems and disadvantages could arise by removing a sealing member consisting of a screw cap from a sample container.

Devices and methods for providing a passage in a stopper of a container of a fluid sample, the passage being intended to allow the withdrawal of the sample, without removing the stopper have been known, however, in the art. A device and a method of this kind are disclosed for example in the international patent disclosure publication WO87/05208 as comprising a sleeve designated as cannula and including a pipe bounded at one end by an oblique curved surface so as to form a prong. The other end of the pipe merges with a seating for receiving a collecting vessel of a suction device. For sucking the liquid sample out of the container, the prong of the sleeve or cannula is stuck through the stopper. Subsequently, the suction hose of the suction device is stuck through the pipe. However, the asymmetric shape of the prong of the pipe has the effect, that the pipe will tend to deviate from the axis of the stopper when it is stuck into the latter so that the sleeve or cannula and its seating will not get properly positioned. This deflection will be of particular disadvantage if the insertion of the sleeve or cannula is to be performed automatically, by mechanical means and without manual aid. Even though claim is made in the cited publication that the particular shape of the pipe prong will avoid or at least greatly reduce the risk of cutting pieces off the stopper, considerable danger still remains, that the hollow pipe with its sharp end will act like a hollow punching tool and will cut particles off the stopper. This is particularly likely to occur at the rear end of the oblique surface forming the prong. Particles cut off the stopper may then fall into the sample liquid while the pipe penetrates through the stopper and/or if the suction hose is pushed through the pipe, thus hindering the suction of the liquid sample and/or the analysis of the sample performed subsequently.

SUMMARY OF THE INVENTION

Hence from what has been explained heretofore it is apparent that there is still needed an apparatus and a method for providing a passage in a sealing member of a container of a fluid sample, particularly in a sealing member consisting of a stopper, which apparatus and method do not have the drawbacks and limitations of the prior art. More particularly, it is an object of the present invention to provide an apparatus and a method for creating a passage in the sealing member of a container of a fluid sample by inserting a sleeve into the sealing member for defining the passage in such a manner, that the axis of the sleeve may easily be made parallel and coaxial with the axis of the sealing member and that no particles will be cut off the sealing member.

The foregoing and other objects are attained in accordance with the invention by creating an apparatus for providing a passage in a sealing member of a container of a fluid sample, the passage to be defined by a sleeve penetrating the sealing member. There is provided a sticking or piercing tool comprising a spike, and the sticking tool is displaceable along a displacing path and the spike is provided with a pointed end portion and adapted to be inserted into the sleeve, the sticking tool being further adapted to engage the sleeve, so as to allow the spike together with the sleeve to be pushed into the sealing member and the spike to be withdrawn afterwards from the sleeve.

A further object of the invention is attained by creating a method for providing a passage in a sealing member of a container of a fluid sample, the passage being defined by a sleeve penetrating the sealing member. In this method a sticking tool comprising a spike provided with a pointed end portion is used and the spike is slid through said sleeve and together with the sleeve it is pushed through the sealing member, and the spike is subsequently withdrawn from the sleeve, while the sleeve is left inside the sealing member.

The sleeve has a through-going axial hole that defines, after the insertion of the sleeve into the sealing member, the passage allowing to pass a fluid conduit of a suction device. The end of the sleeve to be first inserted into the sealing member will be referred to as the front end, the other end of the sleeve as the rear end.

A further object of the invention is attained by a sleeve to be stuck through a sealing member of a container of a fluid sample, wherein the sleeve comprises a tubular portion having a front end adapted to be pressed through the sealing member and a rear end adjoined by an enlargement and wherein said front end of the sleeve comprises an outer edge rotationally symmetrical with respect to the axis of the sleeve.

The sleeve may have a body made of one piece and comprising a tubular portion having a circular cylindrical inner surface. At least the major section of the tubular portion of the sleeve may also have a cylindrical outer surface, whereas the front end section of the tubular portion is preferably provided with an outer surface conically tapered toward the front end. At its rear end the sleeve preferably comprises a head portion bounding the enlargement that tapers away from the tubular portion and the front end, which head portion may also be adapted to function as a rest on the sealing member. The enlargement may preferably comprise a funnel-shaped portion for facilitating the insertion of the spike and the subsequent insertion of a suction conduit into the sleeve. The entire tubular portion of the sleeve may be rotationally symmetrical with respect to the axis of the sleeve. The enlargement may also be substantially rotationally symmetrical, not considering any axial, radial or slanted ribs and/or small holes penetrating the sleeve jacket, which may be present. The axial length of the tubular portion is at least equal to the axial length of the central section of the sealing member and preferably somewhat longer, so that the sleeve may at least penetrate the sealing member and preferably protrude slightly beyond the sealing member surface facing the inner space of the container. The length of the tubular portion of the sleeve may typically amount to at least 5 mm, at most 30 mm and for instance 15 to 20 mm. The clear width of the passage defined by the sleeve, i.e. the inner diameter of the tubular portion of the sleeve is preferably made so small, that the fluid sample—for example blood or blood serum—will not flow out through the open passage even if the passage is horizontal, or if the sample container is turned upside down so that the sealing member will be at the bottom. The maximum allowable value of the aforementioned clear width depends on the physical characteristics of the sample fluid, specifically on the surface tension and the viscosity. For the fluids of interest the desired feature, i.e. blocking the outflow, may be achieved by making the clear width not more than 4 mm and preferably not more than 3.5 mm. The clear width should preferably be at least 1 mm, to allow a suitable suction conduit to be pushed through the passage.

The spike may have its major portion substantially cylindrical, not considering any longitudinal groove and transverse hole that may be provided, and thus have a cylindrical bounding surface. The pointed free front end portion of the spike may be cone-shaped or pyramid-shaped, said pointed free end being arranged to lie on the axis of the spike and thus—in a projection parallel to the displacing direction of the spike—in the center of the latter. On the one hand a cone-shaped free end portion of the spike has the advantage that it is rotationally symmetrical with respect to the spike axis and slightly easier to manufacture than a pyramid-shaped end portion. On the other hand, experience has shown that a spike having a pyramid-shaped pointed end portion offers a slight advantage over a spike having a cone-shaped end portion, by the fact, that the force required for sticking spike and sleeve into the stopper is slightly reduced. This is due to the fact, that the more or less sharp edges of the pyramid which diverge from the pyramid point have some cutting effect and facilitate the displacement of stopper material.

Furthermore, the pointed free front end portion of the spike may either have a full cross-section, i.e. a bounding surface without any opening, or an aeration passage opening preferably adjacent to the point of the spike in the tapering surface of the pointed free end portion. One may select and use a spike without or with aeration passage depending upon the kind of the fluid sample and of the type of analyses to be performed, as will be explained more in detail. The substantially cylindrical major portion of the spike intended to be slid through the tubular portion of the sleeve or—more precisely—the cylindrical bounding surface of said substantially major portion may have a diameter smaller by 0.05 mm to 0.2 mm than the diameter of the inner cylindrical surface of the tubular portion of the sleeve. This allows the spike to be properly slid in and out of the sleeve and be accurately centered within the sleeve if inserted thereinto. The sticking tool is preferably provided with spring means comprising at least one spring having an elongated portion and an end portion forming an angle with said elongated portion. This latter portion may extend along the groove and be inserted at least partially thereinto, whereas the end portion of the spring means may protrude into the transverse hole of the spike and be guided therein radially slideably. The spring means may be held and prestressed in a manner to have its end portion and the adjacent section of its elongated portion capable of making radial spring movements, whereby—due to prestressing—the elongated portion will tend to move away from the axis of the spike and out of the groove, and will be able to be pressed by the inner surface of the tubular portion of the sleeve toward the base of the groove and against an elastic restoring force. Furthermore, the spring means is arranged and dimensioned in a manner to allow the spike to be easily slid into the sleeve, to hold the latter firmly enough on the spike by virtue of having a downward looking free front end for avoiding the sleeve from falling off the spike and to allow the sleeve to be easily removed from the spike after having been inserted into the appropriate stopper. More specifically, the holding force produced by the spring means and the friction between the sleeve and the spike and possibly other portions of the sticking tool should be, on the one hand, large enough to overcome the force resulting from the force of gravity and perhaps the force of acceleration acting on the sleeve and tending to remove the latter from the spike while the spike is moved toward the sleeve. On the other hand, the force holding the sleeve on the spike should be smaller than the removing force produced after the insertion of the sleeve into the sealing member by the force of friction between the sealing member and the sleeve and to a slight extent by the force of gravity and perhaps by the force acceleration on the spike.

The angles that the tapering surfaces at the front end sections of the sleeve and the spike include with the axes of the sleeve and spike, respectively, may be at least approximately equal to each other and amount to at most 45°, and have for instance values between 10° and 20°. The axial extension of the substantially cylindrical major portion of the spike must be at least equal to the axial extension of the tubular section of the sleeve and should be adapted to the design of the sticking tool and the sleeve in such a way, that the pointed end portion of the spike—if the latter is in the position in which it is stuck inside the sealing member together with the sleeve arranged on the spike—will protrude beyond the front end of the sleeve. The rear border of the tapering surface of the pointed end portion of the spike should then be preferably very close to the front end of the sleeve and protrude for instance only very slightly beyond the front end of the sleeve. The conical or chamfered outer surface of the end section of the sleeve and the cone-shaped or pyramid-shaped surface at the front end portion of the spike will then be—at least at some axial sections—nearly continuous.

Producing a passage in a stopper serving as sealing member by inserting into it a sleeve comprising a front end having a circular edge lying in a plane perpendicular to the sleeve axis and coaxial with the latter, by using a spike with a pointed front end, allows the insertion of the sleeve into the stopper made of an elastic and for instance rubber elastic material, in such a manner, that the space needed for the sleeve will be created by displacing stopper material without cutting away any such material. The prevention of the cutting away and shearing away of stopper material may be further enhanced by making the distance between the inner surface of the sleeve and the spike—at least at the front end of the sleeve, where the spike protrudes out of the sleeve—as small as possible without causing any large frictional forces between the sleeve and the spike. This may be achieved by matching or adjusting the inner diameter of the tubular sleeve portion to the diameter of the spike in the previously specified manner. Avoiding the cutting away of stopper material eliminates the risk of having fluid sample contaminated by stopper material particles falling into it. The possibility of inserting a sleeve into a stopper by displacing stopper material without cutting away any of the stopper material furthermore contributes to achieving a solid anchoring of the sleeve within the stopper.

Many important blood analyses are performed using blood serum only. Blood introduced into a container may be separated in such cases within the sealed container in a centrifugation and/or sedimentation process. This process is performed in a way that to have the container positioned at the end of the process vertically, with the sealing member on top. The sample container may then be held in a vertical position until the sleeve will have been inserted through the sealing member. After such a preliminary processing the lowermost section of the sample container will contain the blood cake containing blood corpuscles. On top of this blood cake, the sample container will have a section containing blood serum. The inner space of the container will furthermore comprise, between the blood serum and the sealing member, a section free of blood and containing air and/or other gases. The sealing member surface facing the inner space of the sample container will then normally be, at least for practical purposes, free of blood, too. Thus, in a case, in which the sample has been centrifugated prior to inserting the sleeve, one may use a spike having its pointed free end provided with a full cross-section, i.e. no aeration passage.

However, in some types of analyses complete non-centrifugated full blood rather than serum is used. The diagnosis of AIDS, for instance, as presently done, requires full blood analysis. In this case, the sample container contains before the insertion of the sleeve complete homogeneous, non-separated blood. Depending on any prior handling, the case may arise, that blood in the form of liquid and/or froth will extend nearly up to the sealing member. In this case and particularly if the sealing member consists of a rubber elastic stopper, it may be advantageous to provide the sticking tool with an aeration passage going fully or in part through the spike and having its mouth open near the point of the spike. The reasons therefore will be explained below in the description of the various embodiments.

It is also possible to subject the sample container with its blood sample to centrifugation and/or sedimentation after having inserted the sleeve into the sealing member. This would allow for instance to insert a sleeve into the sealing member of the sample container containing full homogenuous non-separated blood, to extract a portion of this blood for subsection to analysis, to submit the sample container with the remaining blood sample to centrifugation so as to separate the blood into blood cake and serum and to extract blood serum for additional analysis.

The sample container normally consists of perfectly transparent and clear mineral glass. The spike is to preferably consist of a hard material, such as steel or another metallic material. The pusher may also consist of a hard and rigid material, for instance a metallic material. The sleeve is by preference also relatively rigid and may consist for instance of a more or less transparent polymer such as polystyrene or butadiene-polystyrene. Particularly in case the sleeve consists of one of the aforementioned two materials and is to be inserted into a rubber elastic stopper, the tubular portion of the sleeve may be provided on its outer surface with a film of pure silicon oil or of another lubricant for facilitating the gliding of the tubular portion into the stopper. However, the sleeve may also have a tubular portion with an outer surface sufficiently smooth and/or consisting of a material more or less self-lubricating so that no lubrication is necessary.

The hose to be inserted through the passage defined by the through-going axial hole of the sleeve for sucking fluid out of the sample container can be relatively week and somewhat flexible, and may consist for instance of more or less clear and transparent polypropylene. Alternately, it may be replaced by a rigid pipe. The vessel of the suction device destined to accommodate the fluid sucked out of the sample container may also consist of a more or less clear and transparent polymer such as polypropylene.

The apparatus may comprise holding and/or transporting means adapted to hold a plurality of sample containers each sealed by means of a sealing member and to also sequentially transport the sample containers with the help of a motor to a processing position, in which the sealing member lies in the displacing path of the spike and sealing member and spike have parallel and preferably aligned axes, so that the spike of the sticking tool together with the sleeve may be stuck into the sealing member. The apparatus may further include driving means comprising a motor for axially displacing the sticking tool back and forth. The apparatus may also comprise motor-driven feeding means for delivering transporting sleeves and for bringing sleeves one after the other in a ready position, making it possible to slide a sleeve onto the spike of the sticking tool passing through it, to enable it to be stuck into the sealing member together with the spike. The various motors preferably consist of electrical motors such as step motors, but may be pneumatical motors or may entirely or partially be replaced by other pneumatical or hydraulical actuating and/or driving means. Versions of the apparatus having motor-driven and/or pneumatically or hydraulically driven means for conveying the sample containers, for displacing the sticking tool and for feeding the sleeves, are adapted to fully automatically provide the individual sealing members of a number of sample containers with sleeves defining the corresponding passages. An operator may then arrange for example a group of sample containers in or on a supporting member of the holding means in a way to have the apparatus insert a sleeve into each of the sealing members and then remove the group of sample containers for further operations. However, it is also possible to integrate such versions of the apparatus into an analyzing system adapted for making fully automatic analyses of the samples. If the samples comprise for instance blood and/or blood serum, the analyzing system may be able to determine the concentrations of different substances present in the blood and thus potentially detect diseased states.

However, there may also be provided a simpler version of the apparatus having no motors but only holding means comprising a supporting member arranged immovably on a frame and adapted to hold one single sample container. Each sleeve may then be slid manually onto the spike. The latter may then be displaced back and forth along the displacing path by a manually operable device.

BRIEF DESCRIPTION OF THE DRAWINGS

Further objects and advantages of the present invention will become apparent from the following detailed description of preferred embodiments by making reference to the appended drawings. There show:

FIG. 1 a schematic, mainly sectional representation of an embodiment of the apparatus for automatically inserting sleeves into stoppers of sample containers;

FIG. 2 the sticking tool of the apparatus according to FIG. 1 drawn to a larger scale;

FIG. 3 a sleeve drawn to the same scale as FIG. 2;

FIG. 10 a side view of a section of a spike having a pyramid-shaped pointed end portion;

FIG. 11 an axial cross-sectional view of a part of a sticking tool, the spike of which comprises an aeration passage;

FIG. 12 a view on that side of the spike shown in FIG. 11 that comprises a mouth of the aeration passage;

FIG. 13 a cross-sectional view of the upper section of a sample container closed with a screw cap; and FIG. 14 a schematic view of a sticking tool attached to a pivotable arm.

DETAILED DESCRIPTION OF THE PREFERRED EMBODIMENTS

Figure 4:
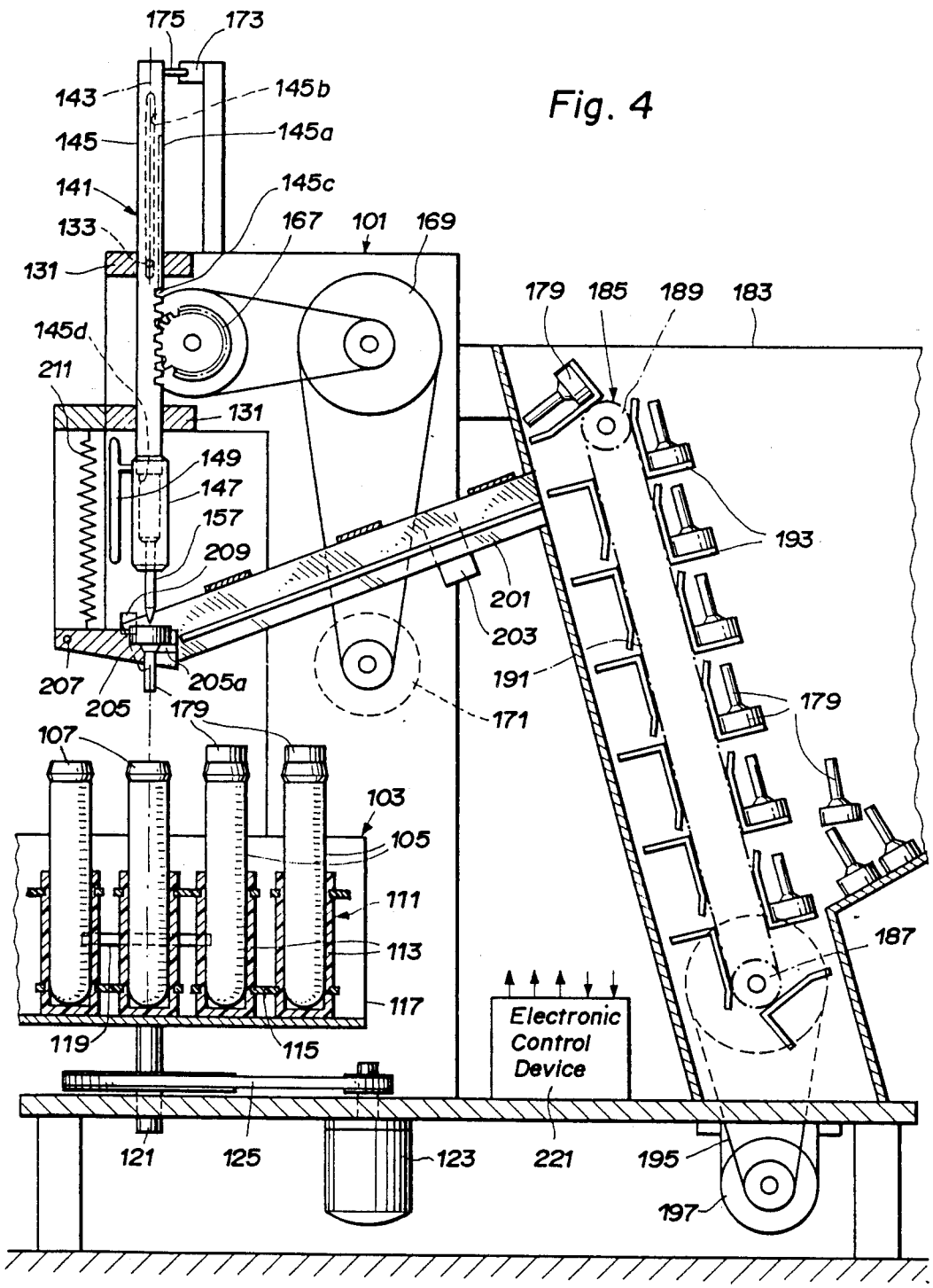
FIG. 4 a schematic representation of another embodiment of the apparatus for automatically inserting sleeves into stoppers of sample containers wherein the sticking tool is shown in its start position.

The apparatus schematically represented in FIG. 1 includes a frame 1 comprising a base plate. A bearing and/or driving means 1' is mounted on the base plate. A circular disk-shaped supporting member 2 is supported on a bearing and/or driving means 1' for rotation around a vertical axis. The supporting member 2 may be, for instance, detachably fastened to a rotatable part of the bearing and/or driving means 1', by means of a fastening member, such as a nut or a quick-locking device, so that it can be fastened and unfastened quickly. The supporting member 2 has a plurality of tubular holders mounted thereon and distributed along the periphery thereof, only the tubular holder disposed in the treating position and designated by the numeral 3 being shown in FIG. 1. Each tubular holder 3 comprises a substantially cylindrical jacket, symmetrical around a vertical axis, and is closed at the bottom and open at the top.

The tubular holders 3 are adapted to hold sample containers 4 consisting each of a substantially cylindrical test glass tube closed at the lower and open at the upper end, the opening on top being sealed gas-tight by means of a sealing member, namely a stopper 5 made of one of the materials mentioned in the introduction, for instance of natural and/or synthetic rubber. The sample container 4 contains a body fluid to be analyzed, such as blood by centrifugation separated in blood cake and serum. The bearing and/or driving means 1' adapted to support and drive the rotatable supporting member 2 also comprise a motor and/or are connected with a motor. The bearing and/or driving means 1', the supporting member 2 and the tubular holders 3 constitute together holding and/or transporting means for holding a number of sample containers 4 and for transporting one container after the other into the treating position.

The frame 1 is provided with guiding means comprising two vertical rods 6 and 7 guiding a carriage serving as tool holder 8 movable upwards and downwards and secured against rotation. The tool holder 8 can be displaced by the action of an electric motor 19 by way of a transmission 21 comprising for instance toothed wheels and a toothed belt, or a pulling chain or belt with or without teeth, or a rope 20. The tool holder 8 has an arm 8a protruding away from the rods 6 and 7 and detachably holding a sticking or sleeve inserting tool 23. The latter is separately shown at a larger scale in FIG. 2 and comprises a spike 11 and a pusher 25, whereby spike and pusher are separate, rigidly connected members, namely a pin and a sleeve. The spike 11 of the sticking tool 23 has a circular cylindrical major portion 11a and at its free front end a conical pointed end portion 11b. The cylindrical portion 11a is provided with a longitudinal groove 11c that extends from the rear end of the cylindrical portion 11a to an end place near the pointed end portion 11b but still at some distance from the latter. The portion of the spike 11 extending from the last mentioned groove end to the free front end of the spike is therefore rotationally symmetrical with respect to the axis of the spike around the entire circumference of the latter and has a full cross-section. The cylindrical major portion 11a is further provided near the lastmentioned end of the groove 11c with a transverse hole 11d, namely a diametrically through-going bore that opens at one end into the groove 11c. The pusher 25 of the sticking tool 23 comprises an axial hole 25a, namely a blind bore. The pusher 25 surrounds the spike 11 coaxially and is bounded at its lower end, i.e. its front end, by an engaging surface 25b forming a right angle with the axis of the spike. The rear end of the pin forming the spike is seated in the hole 25a and attached to the sleeve forming the pusher 25 by a screw not shown or by a press fit connection and/or possibly by welding or soldering. A spring means 10 consists of a piece of wire and has an elongated portion 10a extending from the rear end of the spike 11 along the groove 11c to the transverse hole 11d. The spring means 10 has furthermore an end portion 10b that forms a substantially right angle with the elongated portion 10a, protrudes into the transverse hole 11d and is displaceably guided inside the latter. The section of the groove 11c located adjacent to the rear end of the spike 11 and inside the hole 25a is about equal in depth to the diameter of the wire forming the spring means 10, so that the latter is held there more or less firmly in place. The groove 11c has furthermore a section that begins near the mouth of the hole 25a inside the latter, extends at least to the transverse hole 11d and has a depth somewhat greater than the diameter of the wire constituting the spring means 10. The section of the spring means 10 located outside the hole 25a is free to make limited spring movements in radial direction.

The sleeve 9 shown in FIG. 3 and intended to be inserted into a stopper 5 has a through-going axial hole and a tubular portion, the outer surface of the latter having a circular cylindrical major surface and at its front end a short conical or chamfered surface 9a tapering towards the front end of the sleeve 9. The conically tapering surface 9a constitutes together with the circular cylindrical inner surface 9b of the tubular portion a more or less sharp edge 9c concentric with respect to the axis of the sleeve. The rear end of the sleeve 9 comprises a funnelshaped enlargement 9d having inner and outer surfaces conically enlarging away from the tubular portion and the front end of the sleeve.

Sleeve feeding means comprise a rotatable storage or delivery drum 12 on which a flexible polymer tape 13 is wound up that carries a plurality of sleeves arranged in a row. The sleeve feeding means comprise furthermore a guiding rail not represented in the drawing for guiding the tape 13 unwound from the drum 12. The sleeve feeding means also comprise conveying means including a motor for conveying the tape 13 so that the sleeves carried by the tape 13 are brought to a ready position lying on the displacing path 14 of the sticking tool, the displacing path being in alignment with the axis of the spike 11. The apparatus also comprises a separating device 15 shown schematically in FIG. 1 and comprising for instance a cutting edge or a heated wire. This separating device 15 allows to cut off the tape portion carrying the first sleeve designated by the numeral 9a. from the rest of the tape. The sleeve 9a is held in this ready position on a pivotable, bow-shaped or fork-shaped positioning member 16 until it is seated on the spike 11 if the latter—beginning from its start position shown in FIG. 1—is moved downwards and slid through the sleeve 9a. If the sticking tool is further lowered, the engaging surface 25a of its pusher 25 engages the rear and upper end of the sleeve 9a and pushes the latter downwards, whereby the positioning member 16 is pivoted away. The apparatus comprises further a hold-down member 17 with a bow-shaped or ring-shaped portion and being displaceable along the displacing path 14. The hold-down member 17 represented in FIG. 1 in its start position may then—if the sticking tool has seized the sleeve 9a and moves further down—be moved downwards by a spring loaded catch not shown in the drawing and connected with the tool holder 8 or directly with the sticking tool 23 until the hold-down member 17 reaches the upper surface of the stopper 5 sealing the sample container 4. The sticking tool 23 is then lowered with the carried sleeve 9a so low, that the spike 11 and the sleeve are stuck into the stopper 5 and the spike 11 and the tubular portion of the sleeve will penetrate the stopper. The sleeve 9a attains thereby a predetermined lowermost position in which the outside of the enlargement 9d comes to rest on the stopper 5. The motor 19 is then controlled in a way to have the tool holder 8 and the sticking tool 23 moved slightly upwards and moved afterwards downward a second time, to the predetermined lowermost position. The case may namely arise that the elasticity of the stopper causes a slight springing-back of the sleeve after the first lowering of the sticking tool. The brief subsequent pushing of the sleeve by the sticking tool causes the sleeve to be displaced, at least practically, to the desired position into the stopper in spite of the afore-mentioned springing-back phenomenon. After the brief, second lowering of the sticking tool 23, the tool holder 8 and the sticking tool 23 are moved upward, back to their start position shown in FIG. 1. The spike 11 is drawn out of the sleeve remaining inserted inside the stopper during the phase of upward displacement of the sticking tool. During this phase, the hold-down member 17 holds the stopper 5 in the sample container 4 and the latter in the tubular holder 3, whereas the inserted sleeve is held by static friction inside the stopper. As the spike is pulled out of the sleeve, the hold-down member is also moved upwards to its start position shown in FIG. 1. During and/or after the upward movement of the sticking tool, the disk-shaped supporting member 2 is rotated by such an angle, to have the sample container, whose stopper has been provided with a sleeve, moved away and another sample container moved in the treating position. If the spike 11 has risen above the positioning member 16 another sleeve namely the sleeve identified in FIG. 1 by 9b is brought to the positioning member 16. The process can then be repeated until the stoppers of all the sample containers arranged on the supporting member 2 are provided with passage-defining sleeves.

The motor 19 and the other motors of the apparatus may consist for instance of electric step motors. The apparatus may further comprise at least one limit switch cooperating with the tool holder 8 or with the sticking tool 23 itself for defining the upper and/or lower end position. There may further be provided at least one limit switch or some other detecting means for verifying whether the supporting member 2 is indeed provided with sample containers 4 and/or the sleeve feeding means are indeed feeding sleeves. The motors, limit switches and other detecting means may be electrically connected with an electronic control device for controlling the motors to make sure that the apparatus works in the previously described manner. The operator may then for instance take the sample containers out of the tubular holders 3 or dismount the supporting member 2 together with the sample containers arranged on the supporting member 2, and put the sample containers for instance temporarily into a refrigerator before the analysis or directly to a place designated for performing the analysis of the samples. However, the apparatus could also be integrated into a system adapted for performing automatic analyses.

The apparatus shown in FIG. 4 comprises a frame 101 on which are mounted holding and/or transporting means 103 for holding a plurality of sample containers 105 each of which is sealed with a sealing member realized as a stopper 107. The holding and/or transporting means 103 comprise a movable supporting member 111 with a row of tubular holders 113, whereby the supporting member may comprise many more tubular holders than shown in FIG. 4. Each holder is closed at the lower end by a bottom and open on top and adapted for detachably holding a sample container. As it can be seen particularly clearly in the FIGS. 6 and 7, each tubular holder 113 is provided near its lower and upper end with an annular groove 113a. Adjacent tubular holders 113 are pairwise connected by linking members 115 which are omitted for the sake of clarity in FIG. 7 but one is visible in FIG. 8. They consist of thin, elastically deformable plates having a hole for each of the two tubular holders and being detachably latched in the grooves 113a, whereby the linking members 115 are pivotable around the tubular holders 113. The supporting member 111 constitutes, thus, a kind of chain. A guide channel 117 only schematically represented in FIG. 4 comprises a bottom section for slideably support the bottoms of the tubular holders 113 and lateral sections for guiding a portion of the supporting member on two opposed sides and keeping the sample containers in vertical positions. Two gripping and transporting members, 119 that can be seen particularly well in the FIGS. 7 and 8 consist of toothed wheels mounted on shafts 121 rotatably supported in the frame 101 around a vertical axis. The gripping and transporting members 119 are adapted to grip together with a pair of teeth a tubular holder 113. An electric step motor 123 is connected, by way of a transmission 125 comprising toothed wheels and toothed belts and shown only simplified in FIG. 4, with the shafts 121 of the two gripping and transporting members 119 for rotating the latter in opposite directions and transporting thereby the supporting member 111 along the guiding channel 117. The supporting member may be supplied from not shown supply means and for instance be unrolled from a reel.

Guiding means comprise two bushes 131 mounted above the guide channel 117 on the frame for guiding a sticking tool 41 having an axis 143 displaceable along a displacing path being in alignment with said axis 143. The sticking tool comprises a shaft 145 with a substantially cylindrical major portion 145a that penetrates the bushes 131 and is also secured against rotation by means comprising for instance at least one pin 133 on one of the bushes 131 and protruding into an axial groove 145b of the shaft portion 145a. A row of teeth 145c is milled or otherwise provided on one side of the shaft portion 145a so that the latter—or more precisely—its section comprising the teeth constitutes a toothed rack. The shaft 145 comprises a thinner cylindrical portion 145d disposed at the lower end of the portion 145a and below the bushes 131. The lower end of the shaft comprises a short conically tapering or chamfered end portion. A pusher 147 that can be seen particularly well in the FIG.

Figure 5:
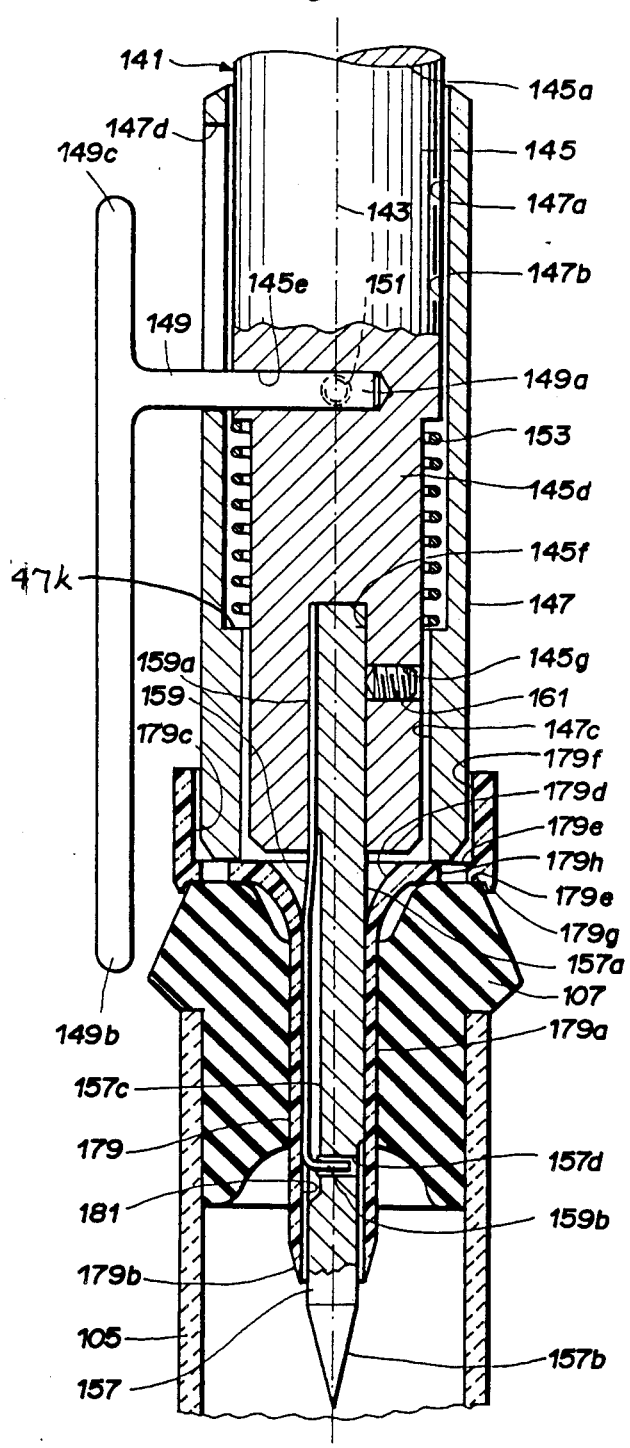
FIG. 5 an axial cross-sectional view drawn to a larger scale than FIG. 4 and showing the upper portion of a sample container, a sleeve and a section of the sticking tool of the embodiment according to FIG. 4 in the phase in which the spike of the sticking tool has penetrated the sleeve and the sleeve has been inserted into the stopper.

5 is axially slideable on the section of the shaft 145 disposed below the bushes 131. The pusher 147 consists of a sleeve whose outer surface is circular cylindrical except for short conically tapering or chamfered end sections on the lower and upper end of the pusher 147. The latter has a through-going axial hole 147a namely a stepped circular cylindrical bore with a wider upper section 147b and a narrow lower section 147c. The inner diameters of these hole sections 147b, 147c are slightly greater than the diameters of the shaft portion 145a and 145d, respectively, so that these two shaft portions guide the pusher with small clearance. The shaft portion 145a is provided near its lower end with a radial bore 145e (FIG. 5). A T-shaped stop and engaging member 149 has a leg 149a fixed in the bore 145e with a screw 151 arranged in a radial, threaded bore of the shaft. The leg 149a penetrates an axial slot 147d of the pusher 147 and is connected at its outer end with the two arms 149b and 149c of the stop and engaging member 149, wherein the arms protrude away from the leg 149a vertically downwards and upwards, respectively. The slot 147d of the pusher 147 serves together with the leg 149a of the stop and engaging member as limit means that define two end positions between which the pusher 147 can be displaced relative to the shaft 145. A helical spring 153 (FIG. 5) is arranged in the free tubular space between the cylindrical surface of the shaft portion 145d and the inner surface of the hole section 147b of the pusher 147. The spring 153 engages the shoulder surface formed by the lower end of the major shaft portion 145a as well as the shoulder surface 147k of the pusher 147 and exerts a downwardly directed force on the pusher 147. The shaft 145 is provided at its lower end with a coaxial bore 145f namely a blind circular cylindrical bore. The spike 157 of the sticking tool 141 is formed by a pin detachably connected with the shaft 145 and comprises a substantially circular cylindrical major portion 157a seated partially in the hole 145f of the shaft 145. The spike has at its free front end a conical pointed end portion 157b, its point or tip lying on the axis of the spike. The spike 157 is substantially identical with the spike 11 and specifically comprises a longitudinal groove 157c corresponding to the groove 11c of the spike 11. Accordingly, the groove 157c begins at the rear end of the spike and ends at a place located on the major portion 157a and at some distance from the rear and of the tapering surfaces of the pointed end portion 157b. The spike 157 also comprises a transverse hole 157d arranged similarly to the hole 11d of the spike 11. A spring means 159 is arranged on the spike 157 in an analogous manner as the spring means 10 on the spike 11 and has an elongated portion 159a running along the groove 157c and an end portion 159b protruding into the transverse hole 157d. The spike 157 and therewith also the spring means 159 is detachably fastened on the shaft 145 by means of a screw 161 arranged in a radial, threaded bore 145g of the shaft 145.

The apparatus comprises a toothed wheel 167 (FIG. 4) supported for rotation by bearing means of the frame 101 and engaging the teeth 145c of the section of the tool shaft 145 serving as toothed rack. The toothed wheel 167 can be driven by way of a transmission 169 comprising toothed wheels and toothed belts by an electric step motor 171. A detector 173 comprising for instance a limit switch with movable tracer is mounted on the frame 101 and adapted to cooperate with a pin 175 or the like attached to the upper end of the sticking tool. The detector 173 and the pin 175 are adapted for determining the start position, i.e. the uppermost intended position of the sticking tool.

In FIG. 5 is also shown a sleeve 179 in a state in which rt has been inserted into a stopper 107. The sleeve is entirely rotationally symmetrical to its axis and defines by its through-going coaxial hole a passage 181. The sleeve 179 comprises a tubular portion 179a with a circular cylindrical inner surface extending to the front end of the sleeve. The tubular portion 179a has a major section with a circular cylindrical outer surface and a short end section with a conically tapering outer surface 179b. The tubular portion 179a is connected at its rear end with a head portion enclosing an enlargement 179c which has—beginning at the rear end of the tubular portion 179a—a funnel-shaped inner surface 179d that is slanted relative to the axis of the sleeve and continuously curved in axial section, a radial inner surface 179e and a circular cylindrical inner surface 179f. The head portion comprises at the outer periphery of its radial section a collar 179g protruding downward in the sleeve position represented in FIG. 5, i.e. substantially axially toward the free end of the tubular portion 179a. The collar 179g is arranged to taper in cross-section toward its free edge and has approximately the shape of a triangle, for example. However, the lower corner of this triangle forming the free edge of the collar is rounded and/or flattened. The radially measured thickness of the free edge of the collar 179g is accordingly significantly smaller than the outer radius of the head portion, namely by at most 20% and for instance by approximately or by less than 10% of said radius. The radial section of the head portion is furthermore provided with two or more through-going holes 179h, namely bores, distributed around the periphery. The sleeve 179 consists of rigid, more or less transparent and clear polymers, for example of polystyrene.

The apparatus comprises feeding means for delivering the sleeves 179 to be inserted into the stoppers 107. The feeding means shown schematically in FIG. 4 comprise a vessel 183 connected with the frame 101 and serving for storing a plurality of sleeves 179 of which only a few are represented. At least the outer surface of the tubular portion 179a of the sleeves has been lubricated with pure silicone oil prior to putting the sleeves into the vessel 183. The vessel has a slanted side wall provided with a channel in which an elevator 185 is arranged. The elevator 185 comprises two rotatably supported rolls 187, 189 with teeth or notches or the like carrying a conveying member 191 comprising at least one endless chain or belt adapted to cooperate with the teeth or notches of the rolls 187, 189. The conveying member is provided with catches 193 distributed along the conveying member, wherein each catch 193 is adapted to catch during its upward movement one of the sleeves 179 stored in the vessel 183. At least one of the rolls 187, 189, for instance the roll 187, is connected by way of a transmission 195 comprising toothed wheels and at least one toothed belt, with an electric step motor 197.

The feeding means comprise furthermore a slanted slide chute 201 with two rails connected to form a kind of channel whose upper and entrance end is arranged near the upper end of the elevator 185. The elevator 185 and the slide chute 201 are designed in such a manner that the sleeves 179 conveyed by the elevator to the slide channel arrive normally into the latter in the intended position, with the tubular portion of the sleeve disposed perpendicular to the sliding direction downwards. The slide chute 201 is, however, provided with a slide control device 203 represented only very schematically and adapted for checking whether the sleeves sliding down the slide chute are in the correct position and—if not—for bringing them into the latter by a movable member. A sleeve 179 lies with sections of the edge of its collar 179g on the rails of the slide chute 201 while sliding down the latter. As the collar 179g has a relatively thin free edge, the weight of the sleeve will cause sufficient pressure for ensuring that the sleeve will indeed slide down the chute even though said weight is relatively small and even though the slide chute rails may be coated with silicone oil that stemming from sleeves previously slid down the slide chute and which may possibly hinder the sliding movement.

At the lower end of the slide chute 201 is arranged a positioning member 205 for positioning each supplied sleeve 179 in a position lying in the displacing path of the sticking tool 141 so that the spike 157 of the latter can be slid during its downward movement into the tubular portion of the positioned sleeve 179. The positioning member is mounted by means of a bearing 207 on the frame 1 pivotably around a horizontal axis. A slot 205a is cut into the positioning member from the side of the latter facing the outlet end of the slide chute 201 so that the positioning member is fork-like. The slot 205a has an upper, wider section adapted for accommodating the upper portion of the sleeve 179 constituting the enlargement 179c and a lower, narrower section dimensioned for letting penetrate the tubular portion 179a of the sleeve 179 and for supporting the sleeve if the positioning member 205 is in its substantially horizontal rest or start position represented in FIG. 4. A spring 211 attached with one end on a part of the frame 101 and engaging with the other end the positioning member 205 exerts a force on the latter pulling it upwards against a stop provided on the slide chute 201 or directly on the frame 101 and defining the mentioned rest or start position of the positioning member. At the lower end of the slide chute 201 is furthermore arranged a detector 209 comprising for instance a light source and a light activated switch, or a limit switch with a mechanical tracer, and adapted for detecting the presence or absence of a sleeve on the positioning member 205.

The apparatus furthermore comprises detecting means not represented in the drawing and adapted for detecting whether a tubular holder 113 being in at least one predetermined position is indeed holding a sample container 105. There may also be provided means for detecting whether the elevator 185 is lifting a sleeve 179 with each catch 193 passing a predetermined point, and for detecting and checking other operational features. The apparatus comprises furthermore an electronic control device 221 electrically connected with the motors 123, 171, 197, the detectors 173, 209 and the further detecting means, the electrical connections being schematically indicated by arrows in FIG. 4. The control device 221 is adapted for controlling the operation of the apparatus. The control device 221 determines for instance the number of rotational steps to be made by the different step motors 123, 171, 197 and ensures for instance that the sample containers held by the supporting member 111 be moved one after the other to the treating position and away from the latter, and that the sticking tool 141 is, from its start position, lowered by a predetermined distance to a lower end position. The control device may comprise a manually operable adjusting means for enabling an operator to adjust and determine the lower end position of the sticking tool, such an adjusting possibility being of particular value if sample containers and/or stoppers of various axial lengths are to be handled.

Now the operation of the apparatus will be described, whereby it is assumed that the supporting member 111 is in the position shown in FIG. 4 so that the second sample container 105—counted from the left—is in the treating position in which the axis of said sample container and of the stopper 107 sealing it is aligned with the axis 143 of the sticking tool 141 and accordingly with the displacing path of the latter. It is furthermore assumed that the sticking tool 141 and the positioning member 205 are in the start positions and that the positioning member supports a sleeve 179 in its ready position as represented in FIG. 4. The pusher 147 is then—relative to the shaft 145 and the spike 157—in its lower end position. The spike portion protruding out of the shaft 145 is in this state in part inside the pusher 147 and in part below the pusher. The motor 171 can now drive the toothed wheel 167 so that the sticking tool 141 is displaced downward toward the sample container 105, which is now in treating position. The part of the spike 157 protruding out of the pusher 147 is then slid into the tubular portion of the sleeve 179 so that it can—in cooperation with the spring means 159—hold the sleeve, while the spike does not yet completely penetrate the tubular portion 179a of the sleeve. At the same time, the front end of the pusher 147 is inserted into the enlargement 179c. If the sticking tool has reached this position and is further displaced downwards, the arm 149b of the stop and engaging member 149 engages the positioning member 205 and swings the latter downwards. The sleeve 179 positioned before by the positioning member is then moved downward and out of the slot 205a of the positioning member. The pusher may possibly have been braked and shifted already somewhat backwards relative to the spike when the pusher has been inserted into the enlargement 179c of the sleeve 179 and when the stop and engaging member 149 has started to engage the positioning member 205. When the sleeve comes in contact with the stopper 107 sealing the sample container 105 held in treating position, the stopper temporarily stops the downward movement of the sleeve 179 and of the pusher 147 engaging the radial inner surface 179e of the sleeve enlargement, so that the spike 157 is—during the further downward displacement of the sticking tool—displaced downward both relative to the pusher 147 and to the sleeve 179. The shaft 145 and the spike 157 then reach positions, relative to the pusher 147 and the sleeve 179, in which the leg 149a of the stop and engaging member 149 engages the pusher surface defining the lower end of the slot 147d, so that the pusher is now—relative to the shaft 145 and spike 157—in its upper end position. The pointed end portion 157b of the spike 157 protrudes then out of the sleeve while the spike already begins to enter the stopper 107. During the further downward movement of the sticking tool, the pointed end portion 157b of the spike is moved into and through the stopper, while the pusher 147 also pushes the sleeve 179 through the stopper 107 until the radial section of the head portion of the sleeve comes to rest on the stopper, and the spike 157 and the sleeve 179 reach their predetermined, lowermost positions represented in FIG. 5.

The electronic control device 221 now reverses the rotational direction of the motor 171 so that the shaft 145 and the spike 157 of the sticking tool 141 are raised slightly, for instance five to ten millimeters. The sleeve 179 may then spring back, i.e. move slightly upward because of the elasticity of the stopper 107. After the partial rise, the rotational direction of the motor 171 is reversed so that the shaft 145 and spike 157 are again lowered to the predetermined, lowermost position. This lowering of the shaft taking place after the partial rise of the shaft serves again to push the sleeve 179 and compensate substantially for the springing-back of the sleeve 179. Afterwards, the motor 171 raises the sticking tool 141 until it attains again the start position.

During the first phase of an upward movement of the shaft 145, the spring 153 presses the pusher 147 against the radial surface 179e of the sleeve 179, whereby the pressing force exerted by the pusher is decreasing, of course during the upward movement of the shaft. The pusher 147 accordingly engages the radial surface 179e during at least a substantial part of the aforementioned partial rise of the sticking tool and then—if the sticking tool is again displaced upward to the start position—until the spike 157 and the spring means 159 are partially drawn out of the tubular portion 179a of the sleeve 179. Thus, the pusher holds down the sleeve 179 and—because the latter lies with its substantially radial surface opposite the inner radial surface 179e on the upper side of the stopper 107—indirectly the stopper 107 too, during the first phase of the upward movement of the sticking tool. This helps prevent the spike from lifting the sleeve, the stopper, or even the entire sample container during its upward movement.

As mentioned before, the stop and engaging member 149 swings the positioning member 205 downwards against the restoring force produced by the spring 211 during the downward movement of the sticking tool. The two arms 149b, 149c continue then to engage the positioning member until the sticking tool has been lowered to its lowermost position and lifted again afterwards to the height at which the stop and engaging member 149 had previously begun to engage the positioning member 205. This ensures that the positioning member 205 is kept slanted downwards and away from the shaft 145 and the pusher 147 during a part of the upward movement of the sticking tool and does not hinder this upward movement. Afterwards, the spring 211 pulls the positioning member 205 back to its start or rest position. It is noted in this context that it may happen, that a tubular holder 113 being in the treating position is empty, i.e. it holds no sample container. If the sticking tool carrying a sleeve is then lowered to its lowermost position it will of course "find" no stopper there. In such a case, the sticking tool will carry the sleeve again upwards, whereas the stop and engaging member 149 may keep the positioning member 205 in a position allowing the sleeve to be lifted above the positioning member.

Figure 7:
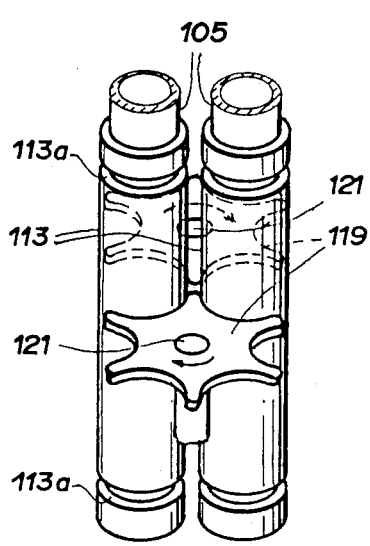
FIG. 7 a schematic oblique view showing a portion of a supporting member with tubular holders supporting sample containers, and gripping and transporting members of the embodiment shown in FIG. 4, the gripping and transporting members being shown a different position than in FIG. 4.
Figure 8:
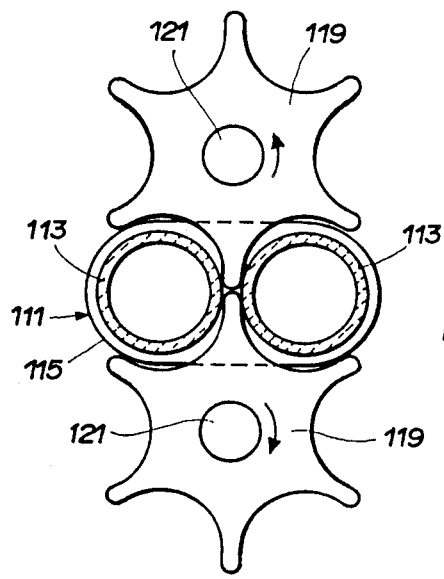
FIG. 8 a schematic top view showing the gripping and transporting members and a portion of the supporting member.

If a sleeve 179 has been inserted into the stopper 107 belonging to the sample container disposed in the treating position and if the sticking tool has been lifted again to its start position, the electronic control device 221 will make the motor 123 rotate the gripping and transporting members 119 in the directions indicated by arrows in the FIGS. 7 and 8 so that the supporting member 111 is moved in FIG. 4 to the right until the next sample container—whose stopper is to be provided with a sleeve—has reached the ready position. The control device furthermore controls the motor 197 in a way to make the elevator 185 deliver another sleeve 179 to the entrance of the slide chute 201 and to have this sleeve slide down the latter and to arrive onto the positioning member 205. After that, a new cycle of operation may begin. The apparatus is thus capable to insert, fully automatically, a sleeve each into the stoppers of a plurality of sample containers. If disturbances or irregularities should occur during the operation, they will normally be detected by the detectors 173, 209 and the other mentioned detection means. The electronic control device can then—dependent on the kind of disturbance or irregularity —undertake counter-measures, or stop the operation and/or give an alarm signal.

It is now assumed that sleeves 179 have been inserted in the stoppers 107 of a plurality of sample containers 105 held by supporting members 111. It is noted in this context, that one can easily separate a supporting member with the required number of tubular holders 113 from a long "stock" supporting member by removing one of the linking members 115. The supporting member 111 carrying the sample containers whose stoppers 107 have each been provided with a sleeve 179 may then be brought by the operator—possibly subsequent to an intermediate storage in a refrigerator —to a place destined for analyzing the sample using appropriate equipment. However, as mentioned in the introduction, the apparatus represented in FIG. 4 may also be integrated into a system for performing automatic analyses. Such a system could then comprise transporting means for transporting the supporting member 111 carrying sample containers having stoppers 107 provided with sleeves 179 to an analyzing station.

Figure 6:
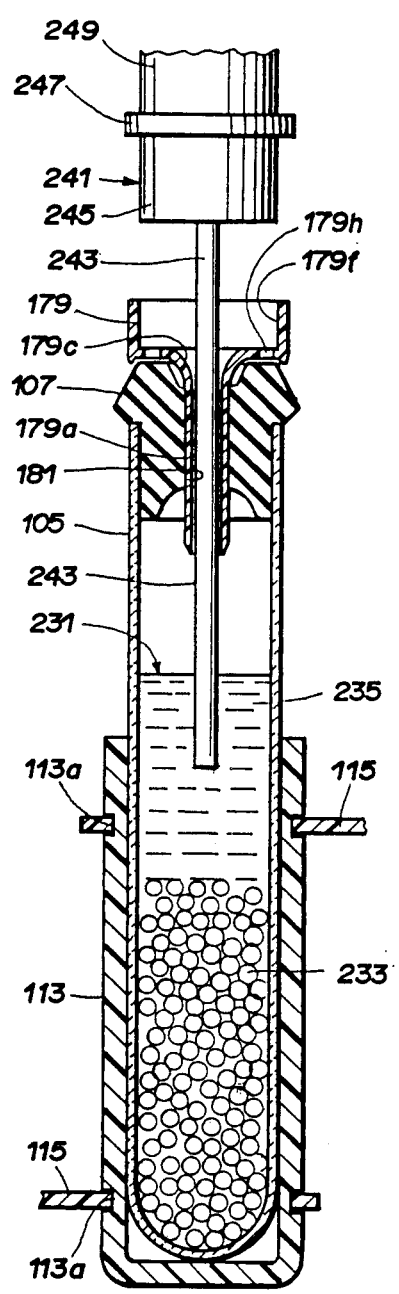
FIG. 6 an axial cross-sectional view of a sample container having its stopper provided with a sleeve operatively connected with a suction device and drawn to a smaller scale than FIG. 5.

The sample contained in the sample containers 105 shown in FIG. 6 is designated by the reference numeral 231. The sample 231 may consist for instance of blood having been subjected in the sample container to centrifugation and/or sedimentation before the insertion of the sleeve, to separate the solid components of the blood from the blood serum. The lower section of the sample container then comprises a blood cake 233 with blood corpuscles, the middle section of the sample container blood serum 235 and the uppermost section of the sample container air and/or other gases. In FIG. 6 is also represented—very schematically—a suction device 241 with a fluid conduit 243 consisting for instance of a somewhat flexible hose of more or less transparent and clear polypropylene. The outer diameter of the conduit 243 should then be so much smaller than the inner diameter of the tubular portion 179a of the sleeve 179, that the conduit may be passed easily through the passage 181 defined by the sleeve, and that a clearance will remain all along the passage between the inner surface of the sleeve and the conduit 243, to enable air to enter from the surroundings into the sample container during the sucking process. The suction device 241 may be designed in various ways dependent on the kind and degree of automatization of the method of analyses used. The suction apparatus 241 may comprise for instance at its lower end a collecting vessel 245 consisting of more or less transparent polypropylene and connected by coupling means 247, such as a bayonet coupling, with a pump member 249 comprising for instance a cylinder and a manually displaceable piston. The collecting vessel 245, or at least its lower portion, may have a cylindrical shape and be designed so that it can be inserted into the section of the sleeve enlargement 179c having the cylindrical inner surface 179f and be then seated there sufficiently firmly to be held by the sleeve. The upper portion of the sleeve enlargement 179c can thus serve as seating for the collecting vessel 245.

The sucking process may be performed for instance by bringing the suction device 241 into a position in which the fluid conduit 243 passes through the passage 181 into the sample, and the collecting vessel 245 is outside the sleeve 179. The desired amount of the sample 231 can be sucked out of the container into the collecting vessel 245. The latter can then be inserted into the upper portion of the sleeve enlargement. As the collecting vessel 245 may fit more or less gas-tight into the cylindrical inner surface 179f of the sleeve 179, the air contained inside the cylindrical portion of the enlargement 179c may—during the introduction of the collecting vessel 245 into the sleeve enlargement 179c—flow out through the holes 179h, through a gap disposed between the upper side of the stopper 107 and the lower side of the radial sleeve head portion and finally through a space disposed between the collar 179g and the stopper surface encompassed by the collar. The aforementioned gap exists because the sleeve has kept on springing back slightly after the described second pushing of the sleeve. The gap is shown in FIG. 6, for the sake of clarity, with exaggerated thickness, the latter being for instance in reality of the order of magnitude of one tenth of a millimeter for outer diameters of the sample container 105, and within the range of 15 mm to 20 mm, for example, for the head portion of the sleeve.

The collecting vessel 245, after insertion into the upper, cylindrical portion of the sleeve enlargement 179c, may be separated from the pump member 249 by detaching the coupling means 247. The collecting vessel 245 may comprise at its connection with the conduit 243 a filter means and/or a check valve to prevent the sample sucked into the collecting vessel from flowing back into the sample container 108. The more or less perfect transparencies of the glass sample container 105, the sleeve 179, the fluid conduit 243 and the collecting vessel 245 allows visual surveillance of the sucking process and of the sample sucked into the sample collector 245. The collecting vessel 245 seated inside the sleeve enlargement may then be temporarily sealed with a removable cover or coupled with a coupling or left open, dependent upon the type of the analyzing equipment used and upon the intended next operation. To be sure, it is not necessary to use a suction device comprising a collecting vessel seatable inside the sleeve. The suction device could comprise for instance a laboratory pipette with a compressible balloon and a sucking conduit without collecting vessel. If the sample is analyzed using an automatic system, the suction device of the latter normally comprises no collecting vessel to be seated in the enlargement of the sleeve. However, there also exists the possibility to use automatic standard analysis combined with supplemental analysis performed by the operator. In any case, the use of sleeves allowing to seat therein collecting vessels, or possibly other members, or means for treating the sample, increases the versatility of the apparatus and of the sample containers whose stoppers have been provided with sleeves.

Figure 9:
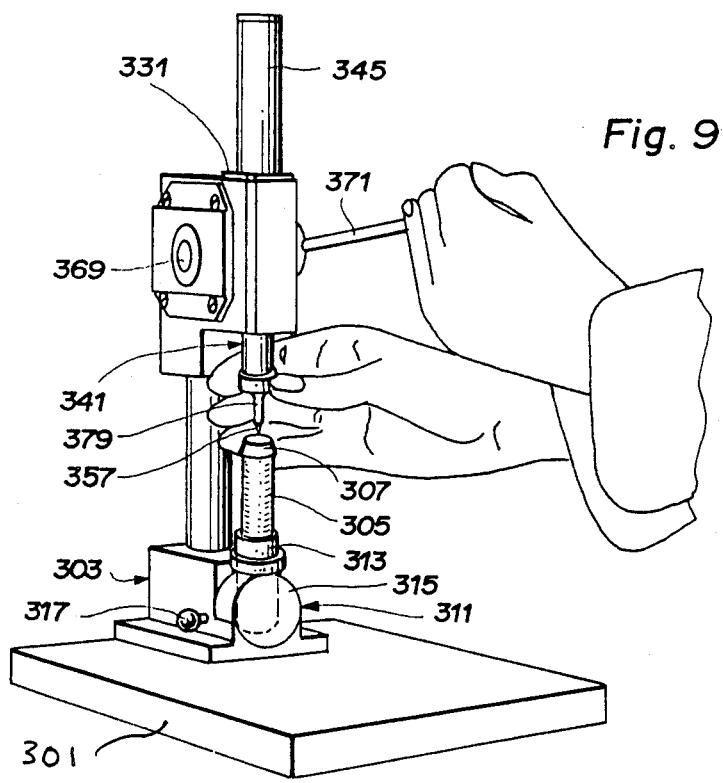
FIG. 9 an oblique view of an embodiment designed to be operated manually.

The apparatus represented in FIG. 9 comprises a frame 301 and holding means 303 for holding a single sample container 305 sealed by a stopper 307. The holding means 303 comprise a tubular holder 313 for accommodating the lower portion of the sample container 305. The tubular holder 313 is seated in a head 315 supported pivotably around a horizontal axis in a block of the frame 301. If the head 315 is in the treating position shown in FIG. 9, the sample container is vertical. The head can also be pivoted into a position in which the axis of the tubular holder 313 is tilted for allowing to insert and remove a sample container. The apparatus comprises means not shown in the drawing for latching the head 315 in the position shown in FIG. 9 and possibly also in the other mentioned position and allowing to unlatch the head by applying a large enough torque onto it. There is furthermore provided a fastening member 317 allowing to remove, replace and fasten again the head 315 so that heads for sample containers of various diameters may be mounted.

Guiding means comprise two bushes 331 of which only the end of the upper one is shown in FIG. 9 and which are fastened to a portion of the frame 301 and are effective to guide the shaft 345 of a sticking tool 341 in the manner the bushes 131 of the apparatus according to FIG. 4 guide the shaft 145. The shaft 345 comprises furthermore a section provided with a row of teeth not represented in FIG. 9 corresponding to the row of teeth 145c, and constituting a toothed rack. The apparatus shown in FIG. 9 also comprises a toothed wheel not shown and engaging the teeth of the shaft 345 in the manner the wheel 167 engages the teeth of the shaft 145. However, in contrast to the toothed wheel 167, the toothed wheel of the apparatus according to FIG. 9 is not driven by a motor but fastened on a rotatably supported crank shaft 369 connected with a crank handle 371, to enable manual rotation of the toothed wheel. The sticking tool 341 comprises a spike 357 rigidly fastened inside an axial blind hole of the lower end of the sticking tool shaft 345 and provided with spring means arranged in a manner analogous to the spring means 10 and 159 of the previously described apparatuses. FIG. 9 also shows a sleeve 379 to be inserted into the stopper 307.

The apparatus represented in FIG. 9 is adapted for manual operation. It is assumed that the head 315 is at first in a position in which the axis of the tubular holder 313 is tilted. The operator can then insert a sample container 305 into the tubular holder, pivot the head 315 into the treating position, slide a sleeve onto the spike 357 with one hand and rotate the crank handle 371 with the other hand to move the sticking tool 341 downward and to stick the spike and the sleeve into the stopper 307. The operator can then rotate the crank handle in the opposite direction for partially lifting the sticking tool. The operator may then again lower the sticking tool for a second pushing of the sleeve 379 into the stopper 307 in a manner analogous to that made in the automatic apparatuses previously described. After the second pushing, the operator may lift the sticking tool entirely, i.e. back to the start position, for pulling the spike out of the stopper and the sleeve. While the spike is pulled out of the sleeve, the operator may manually hold and press down the sleeve and the stopper. Then, the operator can swing the head 315 back into the position in which the axis of the tubular holder 313 is tilted and remove the sample container having now its stopper provided with a sleeve.

The spikes 11, 157, 357 may be replaced by the spike 457, part of which is represented in FIG. 10. The spike 457 comprises a substantially cylindrical portion 457a and a pointed end portion 457b. The latter differs from the end portion of the spikes 11, 157, 357 in that it is pyramid-shaped.

The sticking tool 541 parts of which are represented in the FIGS. 11 and 12 has an axis 543 and comprises a shaft 545, a spike 557 fastened inside the shaft and the spring means 559. The spike 557 comprises a substantially cylindrical portion 557a, a pointed end portion 557b consisting of a cone, a groove 557c, and a transverse hole 557d consisting of a blind bore, and is substantially rotationally symmetrical with respect to the axis 543 of the tool 541. A spring means 559 is arranged similarly to the spring means 10 and 159. The sticking tool 541 furthermore comprises an aeration passage 565 having a portion 565a extending parallel to the axis 543 on one side of the latter and through the spike 557. The portion 565a of the aeration passage 565 opens at one end into the conical surface of the pointed end portion 557b of the spike 557 forming the mouth 565b. The aeration passage 565 also comprises a portion 545 extending from the spike end disposed inside the shaft, through the latter and to the rear end of the shaft. The end of the aeration passage disposed at the rear end of the shaft 545 is connected with an aeration and suction device 573 by way of a flexible conduit 571.

The parts of the sticking tool 541 represented in the FIGS. 11, 12 may replace the corresponding parts of the stiking tool 141 or—with appropriate adaptations—of the sticking tool 23 or 341. The sticking tool 541 may then be operated in a generally similar manner as the sticking tools 23, 141, 343. However, as already mentioned in the introduction, a sticking tool provided with an aeration passage—such as the aeration passage 565—is particularly useful for the analysis of complete, nonseparated blood. In this case the sleeves will be inserted into stoppers of sample containers not yet subjected to centrifugation. It may then happen that—depending on the previously occured handling of a sample container—blood or possibly some type of blood froth containing air and/or other gases will extend at least approximately as far as the stopper sealing the sample container. In the course of inserting a sleeve into the stopper by means of the sticking tool, the central portion of the stopper will get temporarily deformed and pushed towards the inner space of the sample container. This stopper deformation will slightly reduce the volume of the inner space of the sample container and thus increase the fluid pressure in the sample container. Assuming now that a spike without aeration passage, such as for instance the spike 157, is used, it can happen that the increase in fluid pressure will cause blood to enter into the gap between the inner surface of the tubular portion of the inserted sleeve and the cylindrical portion of the spike. The blood could then come in contact with the spring means arranged on the spike. If the spike is subsequently pulled out the inserted sleeve and pushed through another sleeve to be inserted into the stopper of another sample container, there would be some risk that said other sleeve might get contaminated by the blood stemming from the first of the sample con By using the sticking tool 541 having a spike 557 containing the aeration passage 565, the risk for such can be eliminated for all practical purposes. As a matter of fact, the aeration passage 565 in cooperation with the aeration and suction device 573 makes it possible to have any increase in fluid pressure resulting from the insertion of the spike 557, together with a sleeve arranged thereon, into a stopper, to be compensated by an outflow of air against ambient atmospheric pressure, as soon as the pointed end portion 557b will protrude out of the inside of the stopper and into the inner space of the sample container. Similarly, as the sleeve reaches the inner space of the sample container, no excess pressure will build up in said inner space. Accordingly, no blood will be pressed into the sleeve. By using the spike 557, it can possibly happen that the point or tip thereof—i.e. the lowermost section of the pointed end portion 557b—will come in contact with blood and a thin film of blood will adhere on the spike point. However, this implies practically no contamination risk because the point of the spike does not come in contact with the inner surface of the sleeve during the withdrawal of the spike. If the spike 557 is then pushed into the stopper of the next sample container, the pointed end portion 557b will get cleaned by this stopper. Any blood getting thus onto or into the upper portion of the stopper can cause no harm because it will remain on the outside of the sleeve and will be protected by the latter against the sourroundings. It is possible, to be sure, to have some blood get into the aeration passage 565 while the pointed end portion 557b of the spike 557 is inside a sample container. Such blood, however, cannot cause any contamination either, because the aeration and suction device 573 is adapted to suck such blood out of the aeration passage 565 during the sucking phase that takes place in the time interval lying between the withdrawal of the spike from one stopper and its insertion into another stopper.

The sample container 605 partially represented in FIG. 13 consists of a glass tube closed by a bottom at the lower end not shown in FIG. 13, the glass tube comprising near its upper, open end a portion provided with an outer thread 605a. A sealing member also shown in FIG. 13 is realized as a screw cap 607 consisting of two pieces, namely a screw member 609 and a foil 611. The screw member 609 comprises a central section 609a protruding for instance slightly into the interior of the sample container 605 and provided with a throughgoing hole 609d coaxial with the sample container 605. The hole comprises a cylindrical bore and it may comprise at its upper end a conical enlargement. The screw member 609 comprises furthermore, a ring or tubular section 609c with an inner thread 609b screwed onto the outer thread 605a of the sample container. The foil covers the upper side of the screw member 609 and closes the hole 609d thereof. The screw member 609 consists of a thermoplastic polymer not as elastic as rubber but capable of sufficient elastic deformation for achieving—in conjuction with an appropriate design—a tight sealing of the sample container. The screw member may consist for instance of polypropylene or of one of the other polymers mentioned in the introduction. The foil 611 consists of a metallic material and is connected with the screw member by means of an adhesive, for example.

The sample container 605 closed off by the cap 607 may comprise a fluid sample. If the cap 607 is to be provided with a passage for enabling the subsequent extraction of fluid, a sleeve for delimiting the passage may be pushed through the cap. The sleeve may have a shape similar to that of the sleeves 9 or 179 and similarly comprises a cylindrical tubular portion and an enlargement. The outer diameter of the tubular portion of the sleeve may be at least approximately identical with the inner diameter of the bore being part of the hole 609d, with the result that the tubular portion of the sleeve will fit radially inside the bore and will be—after its insertion—firmly and reasonably tightly connected with the cap. The sleeve may be inserted into the cap by means of apparatus comprising a sticking tool and a spike. Such apparatus may be designed similar to any apparatus previously described in conjuction with the various figures. Lowering the sticking tool with its spike carrying the sleeve to be inserted, will enable the pointed end portion of the spike to penetrate into the cap 607 and to create a hole in the foil 611. By further lowering the sticking tool the tubular portion of the sleeve will penetrate the hole created, in the foil 611 by the spike as well as the hole 609d already existing of the screw member 609. After the sleeve has been inserted into the cap 607, the spike is pulled out of the sleeve. Thus, the apparatus for inserting sleeves into caps may work similar to any apparatus described in conjuction with the various figures, having in mind that in this case no second pushing of the sleeves will be necessary.

It is apparent from the foregoing that similar or identical apparatuses may be used for inserting sleeves into sealing members, irrespective of whether the sealing member is a stopper, a screw cap or some other type of cap. It is understood that—if necessary—one may replace the sticking tool of an apparatus to fit a new type of sealing member and/or sleeve.

The apparatus represented partially and schematically in FIG. 14 comprises a frame 701 and holding and/or transporting means not shown FIG. 14. The holding and/or transporting means may be similar to one of those represented in the FIGS. 1, 4, 9 and are adapted for holding and possibly transporting one or more sample containers 705 closed by a sealing member consisting for instance of a stopper 707, the sample container and the stopper being represented by dashdotted lines. A crank 767 is pivotably supported by the frame, the pivot axis being horizontal. The crank 767 comprises an arm 767a, the free end of which is detachably holding the shaft 743 of the sticking tool 741. The crank may be driven by a motor or by a handle adapted for pivoting the arm 767a up and down and for simultaneously inserting into the stopper 707 a sleeve not shown. The displacing path of the sticking tool 741 is, in this case not straight but arcuate. If the radius of this sufficiently arc is greater than the needed length of the displacing path, the latter will deviate only little from a straight line. For the types of stoppers intended to be provided with sleeves, said radius should be approximately 25 cm or more. The crank may be arranged, furthermore in such a way that the tangents to said displacement path portion along which the sticking tool is displaced while the spike is inside the stopper be vertical, as nearly as possible.

The apparatus can be modified in many other ways. It is possible for instance to combine features of the various embodiments of the apparatus described in conjunction with the various figures. The dimensions and/or the shapes of the sleeves may be varied. It is possible provide, for example, axial ribs to the outer cylindrical surface of the head portion that bounds the enlargement of the sleeve 179. As a further possibility, one could equip other sections of the sleeve head portion with ribs. The detachable linking members 115 of the supporting member 111 could be replaced by linking members having the form of flexible strips used in conjunction with tubular holders 113 of an integral belt-shaped polymer body. The flexible linking members would then still allow the tubular holders to be pivoted relative to one another around axes parallel to their own axes. The linking members could then be cut or torn for separating one part of the supporting member from the remainder thereof.

As the spikes may conceivably come in contact with the fluid samples while they are pushed through the stoppers, at least apparatus comprising motors and intended for automatic operation may be additionally equipped with a cleaning device for cleaning the spike. In such a case, the spike may be cleaned, for instance, each time it gets withdrawn from a stopper.

The apparatus described so far is adapted for inserting sleeves into sealing members, in particular into stoppers of sample containers containing a sample. However, the apparatus according to the invention could be adapted for inserting sleeves into stoppers in turn inserted into empty sample containers, or into stoppers not even mounted yet on any sample containers. In this case, the samples could be introduced into the sample containers by way of passages defined by the sleeves.

What is claimed is:

1. Apparatus for providing a passage in the elastic sealing member of a fluid sample container, comprising:
    (a) a sleeve (9, 179, 379) arranged in a first position generally in longitudinal alignment with and spaced from said sealing member; and
    (b) sleeve inserting means for forming a through opening in said sealing member and for mounting said sleeve in said through opening, including:
        (1) a spike (11, 157, 357) coaxially arranged relative to said sleeve on the opposite side thereof from said sealing member, the end of said spike adjacent said sleeve being pointed; and
        (2) means (19, 77, 371, 767) for initially displacing said spike toward said sealing member to cause said pointed spike end to progressively extend completely through said sleeve and to subsequently cause both said spike pointed end and said sleeve to completely penetrate said sealing member and extend through the opening formed thereon, said displacing means subsequently displacing said spike in the opposite direction to withdraw said spike from both said sleeve and said sealing member, whereby said sleeve remains in said opening with the interior of the sleeve defining said passage.

2. Apparatus as claimed in claim 1, wherein said sleeve inserting means includes spring means adapted to secure said sleeve against falling off said spike, but to allow said spike and said spring means to be withdrawn from the sleeve after the latter has been inserted into the sealing member.

3. Apparatus as claimed in claim 2, wherein said spike comprises a cylindrical surface provided with a longitudinal groove, and wherein said spring means comprises an elongated portion arranged to extend along said groove and adapted to be pressed at least partially into the groove.

4. Apparatus as claimed in claim 3, wherein said spike contains a transverse hole opening into said groove, and said spring means comprises an end portion arranged to form an angle with said transverse hole and to be slidably guided along the latter.

5. Apparatus as claimed in claim 1, wherein the end of said sleeve adapted to be first pressed into said sealing member comprises an outer edge that is rotationally symmetrical with respect to the axis of said sleeve.

6. Apparatus as claimed in claim 5, wherein said sleeve comprises a first section having a cylindrical outer surface and a second section having an outer surface tapering toward said sleeve end.

7. Apparatus as claimed in claim 1, wherein said spike is elongated and comprises a section having a surface at least substantially parallel to the longitudinal direction of said spike, and wherein said sleeve inserting means comprises a pusher provided with an engaging surface that forms an angle with the longitudinal direction of said spike and protrudes away from the said surface of said spike, said pusher being adapted to engage said sleeve when mounted onto said spike for pushing the latter into said sealing member.

8. Apparatus as claimed in claim 7, wherein said pusher is slideable relative to said spike parallel to the longitudinal axis of said spike, said sleeve inserting means being provided with a spring adapted to apply on said pusher a force directed toward the pointed free end of said spike.

9. Apparatus as claimed in claim 7, wherein said sleeve inserting means comprises limiting means defining two end positions between which said pusher may be displaced relative to said spike.

10. Apparatus as claimed in claim 7, wherein said sleeve comprises at the end remote from said sealing member and enlargement into which said spike is to be first inserted, and wherein said pusher is adapted to enter into said enlargement and to engage therein a surface of the sleeve.

11. Apparatus as claimed in claim 1, wherein said pointed end portion of said spike comprises a point lying in the center of said spike.

12. Apparatus as claimed in claim 11, wherein said pointed end portion of said spike is free of any opening.

13. Apparatus as claimed in claim 11, wherein said sleeve inserting means comprises an aeration passage extending at least in part through said spike and having at least one mouth near the point of said spike adapted to lie outside said sleeve when said spike penetrates said sleeve.

14. Apparatus as claimed in claim 13, wherein said mouth lies on a tapered surface of said pointed end portion of said spike.

15. Apparatus as claimed in claim 1, wherein the passage in the sealing member is defined at least in part by a cylindrical inner surface of said sleeve, and said spike comprises a section having a cylindrical surface the diameter of which is at least 0.05 mm and at most 0.2 mm smaller than the diameter of the cylindrical inner surface of said sleeve.

16. Apparatus as claimed in claim 1, wherein the width of the passage defined by said sleeve is at most 4 mm.

17. Apparatus as claimed in claim 1, and further comprising holding means for holding the container in a treating position in which the displacement path of the spike passes through the sealing member and in which a sleeve mounted on said spike can be pushed into the sealing member.

18. Apparatus as claimed in claim 17, wherein said holding means comprise a movable supporting member adapted to hold a plurality of containers, and means for transporting said sample containers held by the supporting member, one after the other, into said treating position.

19. Apparatus as claimed in claim 18, wherein said supporting member comprises a row of tubular holders pivotably linked by linking members, each tubular member being adapted to removably hold a container, and further wherein said holding means includes gripping and transporting members (119) adapted for gripping a tubular member and transporting it to said treating position and, afterwards, away from the latter.

20. Apparatus as claimed in claim 1, further comprising feeding means for storing a plurality of sleeves and for bringing each sleeve one after the other, in a ready position in which said spike can be inserted into said sleeve.

21. Apparatus as claimed in claim 20, wherein said feeding means include a vessel for storing a plurality of said sleeves, an elevator with a conveying member comprising catches for catching sleeves contained in said vessel, and a slanted slide chute arranged to enable the sleeves elevated by the elevator to slide downward along the slide channel to said ready position.

22. Apparatus as claimed in claim 21, wherein said sleeve includes a tubular portion, said head portion section being provided with a collar protruding substantially axially toward the free end of said tubular portion and adapted to slide along said slide chute.

23. Apparatus as claimed in claim 1, further comprising a frame, and a toothed wheel supported in said frame for rotation, and wherein said sleeve inserting means includes a toothed rack engaged by said toothed wheel for displacing said spike back and forth along the displacing path.

24. Method for providing a passage in a sealing member of a container of a fluid sample, the passage being defined by a sleeve penetrating the sealing member, wherein a sticking tool comprising a spike provided with a pointed end portion is used and wherein the spike is slid through said sleeve and together with the sleeve it is stuck through the sealing member, and wherein the spike is subsequently withdrawn from the sleeve, while the sleeve is left inside the sealing member.

* * * * *